(12) United States Patent
Kesling

(10) Patent No.: US 6,409,505 B1
(45) Date of Patent: Jun. 25, 2002

(54) CENTRALLY ROTATING PERIODONTAL PROBE

(76) Inventor: Peter C. Kesling, 611 W. 250 South, LaPorte, IN (US) 46350

( * ) Notice: Subject to any disclaimer, the term of this patent is extended or adjusted under 35 U.S.C. 154(b) by 0 days.

(21) Appl. No.: 09/863,723

(22) Filed: May 23, 2001

(51) Int. Cl.$^7$ ............................................... A61C 19/04
(52) U.S. Cl. ......................................... 433/72; 433/141
(58) Field of Search ........................... 433/72, 75, 141, 433/146, 147

(56) References Cited

U.S. PATENT DOCUMENTS

| 4,364,730 A | 12/1982 | Axelsson | 433/141 |
|---|---|---|---|
| 4,664,627 A | * 5/1987 | Kyotani et al. | 433/72 |
| 5,199,718 A | 4/1993 | Linder | 604/232 |
| 5,271,734 A | 12/1993 | Takeuchi | 433/72 |
| 5,486,109 A | 1/1996 | Hunter et al. | 433/72 |
| 5,587,284 A | 12/1996 | Brattesani | 433/72 |
| 5,676,544 A | 10/1997 | Urban | 433/147 |
| 5,725,373 A | 3/1998 | Yeh | 443/72 |
| 6,024,564 A | 2/2000 | Kesling | 433/72 |
| 6,116,899 A | 9/2000 | Takeuchi | 433/72 |

* cited by examiner

*Primary Examiner*—Cary E. O'Connor
(74) *Attorney, Agent, or Firm*—Lloyd L. Zickert

(57) ABSTRACT

A centrally rotating periodontal probe for measuring the depth of gingival pockets or sulci, including a handle having a handle-engaging end and a head end, wherein the head end includes a tubular shank rotatably shank rotatably supporting an axle having a substantially planar blunt end.

19 Claims, 2 Drawing Sheets

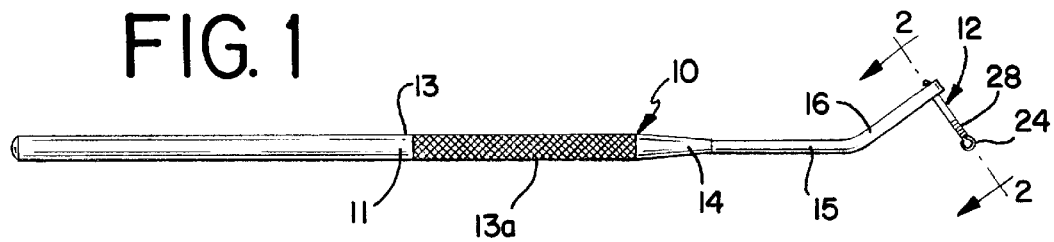
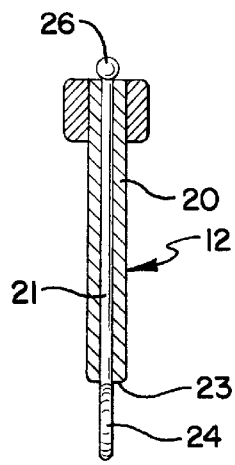
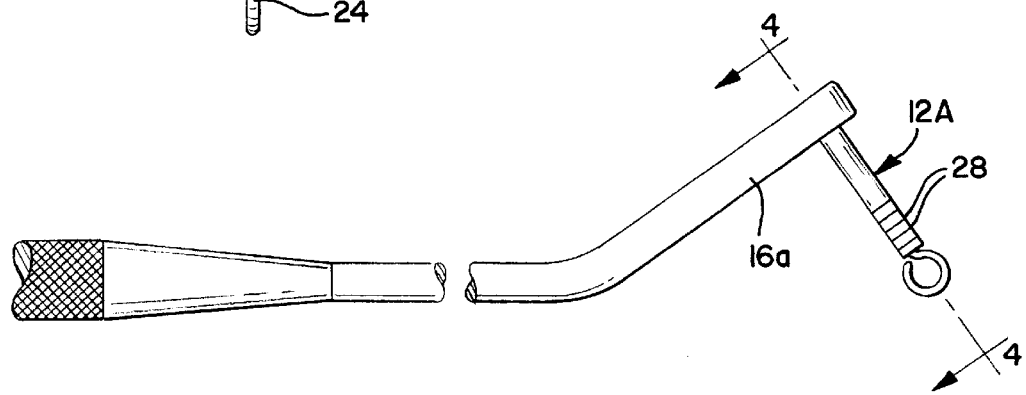
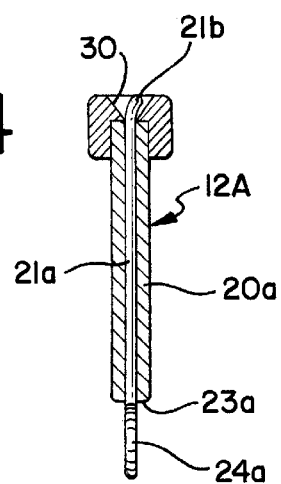
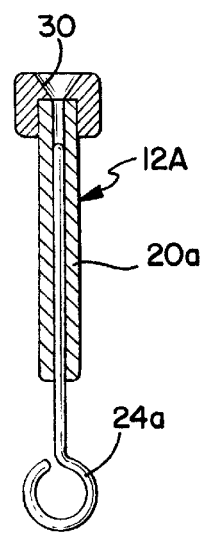

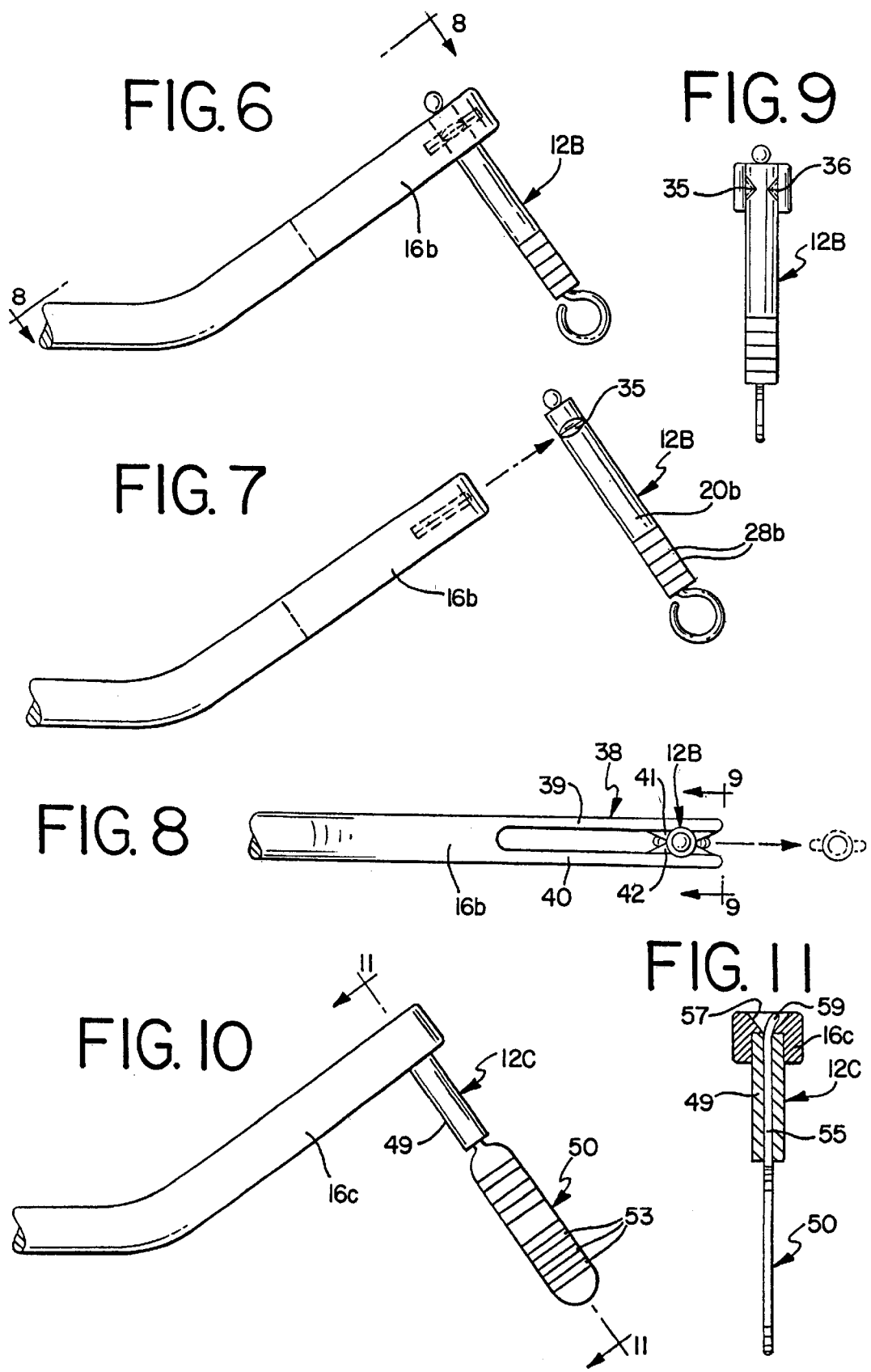

CENTRALLY ROTATING PERIODONTAL PROBE

DESCRIPTION

This invention relates in general to a periodontal probe for measuring the depth of gingival pockets or sulci of a patient's teeth, and more particularly to a periodontal probe having a relatively thin centrally rotating member or end that is provided with a broad or blunt end for insertion into the gingival sulcus to measure the depth of the sulcus.

BACKGROUND OF THE INVENTION

During the examination of a patient's teeth, a dentist will examine the health of the gums or gingiva, and more particularly, manipulate an instrument for measuring the depths of the gingival pockets or sulcii around the teeth. This procedure usually takes place during the cleaning of the teeth.

Heretofore, most periodontal probes used for measuring the gingival pocket depth consisted of a handle having a head angularly related to the handle. The head was in the form of a cylindrical pin that is relatively small in diameter, approximately 0.015 inches (0.4 mm), so that the head can easily slip between the tooth surface and the free gum margin and into the gingival pocket. Such a probe, being relatively small in diameter, when inserted to the bottom of the pocket or sulcus, can be uncomfortable, much like a pinprick each time the bottom is touched. In fact, it would be possible for the dentist to inadvertently penetrate and puncture the periodontal fibers at the bottom of the sulcus, which, while being painful, adds the problem of potentially allowing bacteria into the patient's bloodstream.

Periodontal probes with peripherally rotating heads having broad ends to prevent harm to the patients are known, as shown in U.S. Pat. No. 4,364,730 and my earlier U.S. Pat. No. 6,024,564, the latter of which is incorporated by reference as to the use of the probe. However, they are not easily manipulated because the heads rotate about the outside of a fixed shaft. This also causes unnecessary bulk and friction, which makes the probe difficult to use.

The periodontal probe of the present invention overcomes these problems by providing a probe that promotes comfort to the patient, is easy to use wherein the end of the probe rotates more freely, and the probe substantially avoids the danger of puncturing the periodontal fibers and yet is easy to manipulate by the dentist.

SUMMARY OF INVENTION

The periodontal probe of the present invention includes a centrally rotatable axle or shaft in a tubular housing or bearing carried on the head end of a handle, wherein the axle includes a relatively broad, planar end to engage the bottom of a sulcus. The head of the probe is inserted into a gingival sulcus to measure the sulcus depth at various points of insertion. Slight pressure of the head against the tooth when the probe is moved along the tooth prior to insertion into the sulcus causes the blunt ended axle to rotate and insure the thinnest dimension of the end is always substantially parallel with the tooth to permit easy and comfortable insertion into the gingival sulcus to measure the sulcus depth at various locations around the tooth. This can be done easily without the dentist having to change the horizontal or angular relationship of the handle relative to the tooth as the axle centrally rotates in a tubular shank carried by the handle.

The broad end can be formed by bending the end of the axle or shaft itself into a closed or partially open planar loop with the axle rotatably carried in a tubular housing or bearing having measuring indicia. The end could also be a blade-like shape, which may be substantially square, rectangular, triangular, oval or circular in form that is rigidly mounted on the end of or is integrally formed with the centrally rotating axle. The blade-shaped end could include measuring indicia for measuring the sulcus depth. These ends can have concave surfaces, or be open in their centers to better adapt to convex tooth surfaces.

Additionally, this axle and/or the probe end may be made of metal or plastic and/or other suitable material and be readily removable from the handle for purposes of facilitating the cleaning and sterilization of the probe.

When removable, the axle with its end may be disposed of and replaced with a new axle that is sterile and/or has an end of different configuration. If removable, the axle would have a suitable means to maintain its connection to the handle while in use.

Thus, the axle of the probe would be freely rotatable and provide a thin, relatively flat surface to not only assist in guiding the end around a tooth but also in defining a relatively blunt end that would be comfortable to the patient during its use.

It is therefore an object of the present invention to provide an improved periodontal probe that facilitates its usage to measure sulcus depth easily and enhance patient comfort.

A further object of the present invention is in the provision of a centrally rotating periodontal probe having a blunt end that can rotate with respect to a fixed portion of the probe during the procedure for measuring the depth of the gingival sulcus around a tooth.

Another object of the present invention is to overcome the pain and possible bodily harm associated with conventional periodontal probes having fixed, narrow ends, while providing a probe with a relatively broad centrally rotating end that is more easily and positively rotatable.

A further object of the present invention is in the provision of a periodontal probe having a rotating blunt end and which is broad enough in one dimension to avoid puncturing of the periodontal fibers during the measuring of the depth of the sulcus and narrow enough in the other dimension to slip comfortably between the gingiva and the tooth.

A still further object of the present invention is in the provision of a periodontal probe having a removable, centrally rotating shaft and end that may be disposable to facilitate the sterilization of the handle.

Other objects, features and advantages of the invention will be apparent from the following detailed disclosure, taken in conjunction with the accompanying sheets of drawings, wherein like reference numerals refer to like parts.

DESCRIPTION OF THE DRAWINGS

FIG. 1 is an elevational view of the periodontal probe according to the invention;

FIG. 2 is a greatly enlarged sectional view taken through the head of the probe in FIG. 1 and substantially along line 2—2 thereof;

FIG. 3 is a greatly enlarged broken and fragmentary elevational view of a modification of the probe in FIG. 1 wherein the rotatable axle and blunt end are removable, and particularly showing the head of the probe;

FIG. 4 is a further enlarged sectional view taken through the head of the modified probe of FIG. 3 and substantially along line 4—4 thereof;

FIG. 5 is a sectional view like FIG. 4 and illustrating the axle and blunt end being removable from the tubular shank of the head;

FIG. 6 is a view similar to FIG. 3 but illustrating a further embodiment of the invention wherein the entire head is removable from the end of the probe handle;

FIG. 7 is a view like FIG. 6 but exploded to show the head in removed position;

FIG. 8 is a top plan view of the embodiment of FIG. 6 and taken substantially along line 8—8 of FIG. 6;

FIG. 9 is an end elevational view of the head on the handle as viewed from line 9—9 of FIG. 8;

FIG. 10 is an enlarged elevational view of a further embodiment with the handle broken away; and FIG. 11 is a sectional view taken through the head of the embodiment in FIG. 10 substantially along line 11—11 of FIG. 10.

DESCRIPTION OF THE INVENTION

Referring now to the drawings, and particularly to the embodiment of FIGS. 1 and 2, a periodontal probe 10 according to the invention includes a handle 11 having a head 12 mounted on one end. The handle 11 includes an elongated hand-engaging end or portion 13 having a knurled portion 13a to assist in gripping the handle. A necked down portion 14 extends from the knurled portion to a further diametrically reduced portion 15 that extends in axial alignment with the main portion 11 of the handle. Extending from the portion 15 and at an angle thereto is a handle end portion 16 onto which the head of the probe is mounted at a substantially right angle to the handle portion 16.

The head 12 includes a tubular shank or bearing 20 fixed to the head end portion 16 and extending at a right angle thereto. An axle or shaft 21 is centrally rotatably received in the tubular shank 20. The axle 21 includes a generally planar blunt end in the form of a loop 24 which is disposed to bear on the free end 23 of the tubular shank 20 during rotatable movement relative to the shank. The axle 21 is fixed in position on the tubular shank 20 by an enlarged stop member 26 at the end of the axle opposite the blunt end 24 and is preferably in the form of a ball. Accordingly, the axle 21 and the loop end 24 are rotatably carried in the tubular shank 20 and not removable. The blunt end loop 24 is approximately one millimeter in diameter, while the diameter of the tubular shank 20 is about one-half of a millimeter in outside diameter. Preferably, the loop is circular although it may be substantially polygonal.

Measurement indicia 28 is provided on the tubular shank 20 for measuring sulcus depth. The dimensions of the blunt end and shank are not critical other than they need to be such that they can be easily and comfortably inserted between a tooth face and the gum during the use of the probe for measuring the depth of a sulcus.

During use, the dentist or hygienist can grip the handle with the fingers of their hand and slip the head of the probe between the surface of a tooth and the free gum margin and into the gingival pocket or sulcus until the loop end 24 bottoms at the base of the sulcus so that the depth of the pocket can be measured. The blunt end will automatically rotate and align with the tooth surface to assure the thinnest portion of the end will move along the tooth surface. As seen particularly in FIG. 1, the measuring indicia 28 on the tubular shank in the form of graduated marks can be observed when the head of the probe is bottomed in the pocket of a tooth so as to measure the depth of the pocket or sulcus. It will be appreciated that as the head of the probe is brought against the surface of a tooth, the end loop 24 can easily rotate to parallel the tooth surface so that it can be easily slipped into the gingival pocket. By virtue of the looped end defining a broad or blunt planar end of the head, any penetration of the periodontal fibers is essentially eliminated when the probe head is inserted to measure the depth of the pocket.

A further embodiment of the invention is shown in FIGS. 3 to 5 which differs from the embodiment of FIGS. 1 and 2 in that the axle and blunt end may be removed and thereafter be replaced by a new axle and of possibly even a different configuration. For example, instead of having a looped end the end of the axle could be in the form of a flat or curved paddle which would likewise be rotatable but of a different configuration in accordance with the desires of the user.

The head of this embodiment is generally designated by the number 12A and includes a tubular shank or bearing 20a suitably fixed to the angled end 16a of the handle. Additionally, the end of the handle includes a conically formed notch or recess 30 aligned with the tubular shank 20a and serving to allow the end of the axle 21a opposite the loop end 24a to be bent over as at the tail 21b for retaining the axle and blunt end in mounted relation with the tubular shank. It will be appreciated that with sufficient force the axle and looped end can be removed from the tubular shank as illustrated in FIG. 5 wherein the bent over end 21b will be straightened so that the axle and looped end can be pulled free. Similarly, when mounting a replacement axle and looped end, the axle will be straight, and when it is in bottomed position, that is, the looped end engages the very end 2a of the tubular shank, the opposite end of the axle may be bent over, as shown in FIG. 4, to lock the axle and looped end to the tubular shank. The conical recess 30 permits the bent-over tail 21b the ability to rotate and not extend beyond the very end of the shank and cause patient discomfort as the axle rotates. It will be appreciated that this embodiment would facilitate replacement of the axle and blunt end as above suggested. It should also be appreciated the axle may be made of superelastic wire, such as nickel titanium memory wire, wherein the end holding the axle in place is prebent but would straighten upon removal and be selectively reinsertable after sterilization. 16a of the handle. Additionally, the end of the handle includes a conically formed notch or recess 30 aligned with the tubular shank 20a and serving to allow the end of the axle opposite the loop end 24a to be bent over as at the tail 21b for retaining the axle and blunt end in mounted relation with the tubular shank. It will be appreciated that with sufficient force the axle and looped end can be removed from the tubular shank as illustrated in FIG. 5 wherein the bent over end 21b will be straightened so that the axle and looped end can be pulled free. Similarly, when mounting a replacement axle and looped end, the axle will be straight, and when it is in bottomed position, that is, the looped end engages the very end 23a of the tubular shank, the opposite end of the axle may be bent over, as shown in FIG. 4, to lock the axle and looped end to the tubular shank. The conical recess 30 permits the bent-over tail 21b the ability to rotate and not extend beyond the very end of the shank and cause patient discomfort as the axle rotates. It will be appreciated that this embodiment would facilitate replacement of the axle and blunt end as above suggested. It should also be appreciated the axle may be made of superelastic wire, such as nickel titanium memory wire, wherein the end holding the axle in place is prebent but would straighten upon removal and be selectively reinsertable after sterilization.

Referring now to the embodiment of FIGS. 6 to 9, a head 12B is shown, which may be completely removable from the handle end 16b of the probe, and thereafter replaced by a new head after use with a patient, or the same one may be replaced for use with another patient after it has been suitably sterilized. As seen in FIG. 7, the head 12B has been removed from the handle, while in FIGS. 6 to 9 it is mounted in position on the handle. Similarly, FIG. 8 illustrates the head in solid lines in position on the handle and in dotted lines in removed position from the handle.

The axle and blunt end are permanently mounted and centrally rotatable within the tubular shank in this embodiment in a similar fashion to the embodiment of FIGS. 1 and 2. It should be appreciated the axle and blunt end may be removable as in the embodiment of FIGS. 4 and 5 and that the axle may be made of memory wire. The tubular shank 20b includes opposed indents 35 and 36 at the upper end of the head which coact with detents on the handle during removal and replacement of the head on the handle. As seen in FIG. 8, the handle includes a bifurcated end 38 having arms 39 and 40 that are resiliently separable during insertion or removal of the head 12b. The arms 39 and 40 are provided with suitable cup-shaped detents 41 and 42 for coacting with the indents on the tubular shank of the head 12b and the tubular shank to lock the head in position against rotational, lateral and longitudinal movement relative to the handle end 16b. Accordingly, the head 12B may easily be removed from and replaced onto the handle of the probe. This would facilitate the separate sterilization of the handle and the head or even permit the head to be disposable so that a new head of the same type or of a different type could be used for each patient. Measuring indicia 28b is provided on the tubular shank 20b for measuring pocket depth.

Another embodiment of the invention is shown in FIGS. 10 and 11, which differs from the previous embodiments in that the head, generally designated by the numeral 12C, includes a shorter tubular shank 49 for rotatably carrying the blunt end 50 in the form of a paddle or blade that includes measurement indicia 53 therealong in the form of graduations for measuring the depth of the sulcus.

The blunt end 50 is carried on an axle or shaft 55 that is rotatably mounted in the tubular shank 49. The tubular shank 49 is fixedly mounted at the end of the handle 16c in a similar manner to the embodiment of FIGS. 3 to 5 in that a conical recess 57 is provided in the end of the handle to accept the bent end of the tail 59 of the axle 55 so that the blunt end 50 with the axle 55 can be removed from the tubular shank and either replaced with a new blunt end and axle or replaced after sterilized as in the embodiment of FIGS. 3 to 5. As previously mentioned with the embodiment of FIGS. 3 to 5, the axle may be made of memory wire with a prebent end.

It will be appreciated that the embodiment of FIGS. 3 to 5, other than having the ability to remove the axle and blunt looped end, will otherwise be used by the dentist of hygienist in the same manner as the embodiment of FIGS. 1 and 2. Similarly, use of the embodiments of FIGS. 6 to 9 and FIGS. 10 and 11 will be the same as that of the embodiment of FIGS. 1 and 2. In view of the foregoing, it can be appreciated that the blunt end of the probe may be substantially planar and be in the form of a loop or paddle.

Other objects, features and advantages of the invention will be apparent from the following detailed disclosure, taken in conjunction with the accompanying sheets of drawings, wherein like reference numerals refer to like parts.

The invention is hereby claimed as follows:

1. A rotating periodontal probe for measuring the depth of the gingival sulcus of a patient's tooth by insertion into and/or traversing the gingival sulcus, said probe comprising:
   a handle,
   a tubular shank extending from one end of the handle,
   a centrally rotating shaft received in said tubular shank, and
   a blunt end on said shaft outward of the free end of said shank for engaging the bottom of the sulcus, wherein said blunt end lies on the axis of rotation of said shaft.

2. The rotating periodontal probe of claim 1, wherein the shank is fixed to the handle.

3. The rotating periodontal probe of claim 2, wherein the shaft is fixed against removal from the tubular shank.

4. The rotating periodontal probe of claim 2, wherein said tubular shank includes means to coact with means on the shaft to permit selective removability of the shaft from the tubular shank.

5. The rotating periodontal probe of claim 1, wherein the tubular shank and shaft are selectively removable from the handle.

6. The rotating periodontal probe of claim 1, wherein the tubular shank includes measuring indicia to measure the depth of a sulcus.

7. The rotating periodontal probe of claim 1, wherein said blunt end is in the form of a loop.

8. The rotating periodontal probe of claim 1, wherein said blunt end is in the form of a paddle.

9. The rotating periodontal probe of claim 8, wherein said paddle includes measuring indicia therealong.

10. A periodontal probe for measuring the depth of the gingival sulcus of a patient's tooth by insertion into and/or the transversing of the gingival sulcus or pocket, said probe comprising: a handle having a hand-engaging end and a head at the other end, said head including a tubular shank and an axle rotatably carried by the tubular shank, said axle having a planar blunt end outward of the free end of the shank and lying in the axis of rotation of said axle and rotatable along the surface of a tooth and engageable with the bottom of the sulcus or pocket.

11. The periodontal probe of claim 10, wherein said axle is permanently carried by the tubular shank.

12. The periodontal probe of claim 10, wherein said axle is removably carried by the tubular shank.

13. The periodontal probe of claim 12, wherein the shank includes measuring indicia thereon to measure the depth of the sulcus.

14. The periodontal probe of claim 10, wherein the planar blunt end is in the form of a wire loop.

15. The periodontal probe of claim 10, wherein the planar blunt end is in the form of a substantially flat paddle.

16. The periodontal probe of claim 15, wherein the paddle includes measuring indicia thereon to measure the depth of the sulcus.

17. The periodontal probe of claim 10, wherein the tubular shank is fixed to the handle.

18. The periodontal probe of claim 10, wherein said head is selectively removable from the handle.

19. The periodontal probe of claim 12, wherein the axle is made of nickel titanium memory wire.

* * * * *

UNITED STATES PATENT AND TRADEMARK OFFICE
CERTIFICATE OF CORRECTION

PATENT NO. : 6,409,505 B1
DATED : June 25, 2002
INVENTOR(S) : Peter C. Kesling

It is certified that error appears in the above-identified patent and that said Letters Patent is hereby corrected as shown below:

<u>Column 4,</u>
Line 29, change "2a" to -- 23a --;
Line 40, delete "16a of the handle.
Lines 41-64, delete.

Signed and Sealed this

Fifth Day of November, 2002

*Attest:*

*Attesting Officer*

JAMES E. ROGAN
*Director of the United States Patent and Trademark Office*